United States Patent
Peter et al.

(10) Patent No.: US 7,590,292 B2
(45) Date of Patent: Sep. 15, 2009

(54) INFORMATION-THEORETIC METHOD FOR CLUSTERING AND MERGING IMPRECISE DATA

(75) Inventors: William Peter, Bethesda, MD (US); Don Lemons, Wichita, KS (US)

(73) Assignee: BAE Systems Advanced Technologies, Inc., Nashua, NH (US)

( * ) Notice: Subject to any disclaimer, the term of this patent is extended or adjusted under 35 U.S.C. 154(b) by 588 days.

(21) Appl. No.: 11/228,323

(22) Filed: Sep. 19, 2005

(65) Prior Publication Data

US 2006/0126945 A1 Jun. 15, 2006

Related U.S. Application Data

(60) Provisional application No. 60/610,693, filed on Sep. 17, 2004.

(51) Int. Cl.
*G06K 9/62* (2006.01)
*G06K 9/36* (2006.01)
(52) U.S. Cl. .................... 382/225; 382/284
(58) Field of Classification Search ............... 382/181, 382/225, 228, 284
See application file for complete search history.

(56) References Cited

U.S. PATENT DOCUMENTS

2004/0013292 A1* 1/2004 Raunig .................. 382/128

OTHER PUBLICATIONS

Domingo-Ferrer, et al. "Practical data oriented microaggregation for statstical disclosure control", IEEE, pp. 189-201, 2002.*
Orechovesky Jr. "Single source error ellipse combination", Naval Post Graduate School "Thesis", pp. 1-82, 1996.*
Aldenderfer, M.S., et al., Cluster Analysis, (Sage, Newbury Park), 1984.
Everitt, Brian, Cluster Analysis, (Heinemann, London), 1974.
Jumarie, G. "Relative Information," p. 36, (Springer-Verlag, Berlin), 1990.
Kaufman, Leonard, et al., Finding Groups in Data (Wiley, New York), 1990.
Smith, J.D.H., "Some Observations on the Concepts of Information-Theoretic Entropy Randomness," Entropy, 3, 1-11, 2001.
Ward, J.H., "Hierarchial Grouping to Optimize An Objective Function," J. Am. Statist. Ass., 58, 236-244, 1963.

* cited by examiner

*Primary Examiner*—Daniel G Mariam
(74) *Attorney, Agent, or Firm*—Bingham McCutchen LLP; Robert C. Bertin; Daniel J. Long

(57) ABSTRACT

An information-theoretic method clusters and merges bi-variate normal data or 'error ellipses' lying in a plane. Two or more error ellipses are clustered and then merged into a single error ellipse if the information lost in the merging process is sufficiently small. This criterion is numerically implemented and tested in a code developed for this purpose.

10 Claims, 2 Drawing Sheets

INFORMATION-THEORETIC METHOD FOR CLUSTERING AND MERGING IMPRECISE DATA

CROSS REFERENCE TO RELATED APPLICATIONS

The present invention claims priority to U.S. Provisional Application No. 60/610,693 entitled "Information Theoretic Method For Clustering and Merging Imprecise Data" filed on Sep. 17, 2004 and listing as inventors William Peter and Donald Lemons.

STATEMENT OF GOVERNMENTAL INTEREST

This invention was made with United States Government support under Contract No. MDA 904-01-F-0371 with the Maryland Procurement Office, and the United States Government has certain rights in this invention.

BACKGROUND OF THE INVENTION

1. Field of the Invention

The present invention relates to methods for clustering and merging imprecise data and, more particularly, to methods for clustering and merging of imprecise data in the form of bivariate normal random variables.

2. Brief Description of Prior Developments

Consider the problem of tracking, with an imprecise measuring instrument, the individual positions of a group of fish as they swim around in an effective two-dimensional plane, say, near the surface of a lake. Furthermore, supposing that reflections or rapid swimming during the measurement process cause multiple images of a single fish to be recorded. Because the data is imprecise, each position is represented by a pair of random position variables. Therefore, the problem of eliminating redundant positions referring to a single fish requires solving the equivalent analytical problem of first clustering and then merging multiple bi-variate random variables.

SUMMARY OF INVENTION

Assuming that these bi-variates are normal, the random position associated with each piece of data is completely determined by two means, two variances, and a covariance. Alternatively, each bi-variate normal is represented by a particular "error ellipse", defined as a contour of constant probability density, with given position, size, and orientation.

The present invention is an information-theoretic solution to the problem of clustering and merging error ellipses. In particular, ellipse are used only when such merging loses sufficiently little quantifiable information given that the replacement ellipse preserves the pooled means, variances, and covariances of the original ellipses. Limiting information loss provides a true similarity criterion since only ellipses that are similar in position, size, and orientation are merged. This criterion is robust and reduces to a single Boolean test that can be applied either pair-wise sequentially or all at once to a group of ellipses. It is that using this criterion to merge and thus to eliminate redundancies in or to reduce and simplify bi-variate normal data, but it can also be used to cluster error ellipses without subsequent merging.

Cluster analysis has a long history and a large literature of application in the social and natural sciences as disclosed in Aldenderfer, M. S. and Roger K. Blashfield, *Cluster Analysis* (Sage, Newbury Park, 1984); Everitt, Brian, *Cluster Analysis* (Heinemann, London, 1974); and Kaufman, Leonard and Peter J. Rousseeuw, *Finding Groups in Data* (Wiley, New York, 1990), the contents all of which are incorporated herein by reference J. H. Ward's entropy criteria for hierarchically grouping data, which is disclosed in Ward, J. H., "Hierarchical grouping to optimize an objective function," J. Am. Statist. Ass., 58, 236-244(1963), the contents of which is also incorporated herein by reference, is also relevant to the present invention. However, there are several important structural differences that distinguish typical cluster analysis techniques and the information-theoretic method of the present invention. (1) Cluster analysis groups data conceived as realizations of random variables, whereas in the present invention bi-variate random variables as grouped. (2) Cluster analysis stops at forming groups of data, whereas error ellipses are grouped in order to merge them into a single replacement ellipse. (3) And cluster analysis decides whether or not to group data by inspecting the group's statistical properties whereas in the present invention decisions are made by comparing the means, variances, and covariances of the ellipses to be clustered with those of their potential replacement ellipse.

BRIEF DESCRIPTION OF THE FIGURES

The above described features and advantages of the present invention will be more fully appreciated with reference to the detailed description and appended figures, in which.

DETAILED DESCRIPTION

I. How to Merge Two Error Ellipses

Because each error ellipse in the x-y plane represents a bi-variate normal random variable, each is uniquely described by two means, $\mu_x$ and $\mu_y$, two variances, $\sigma_x^2$ and $\sigma_y^2$, and one covariance $\sigma_{xy}$. The probability density function of such a bi-variate ellipse is $$p(x, y) = \frac{\exp\left[\frac{-1}{2(1-\rho^2)}\left\{\left(\frac{x-\mu_x}{\sigma_x}\right)^2 - 2\rho\left(\frac{x-\mu_x}{\sigma_x}\right)\left(\frac{y-\mu_y}{\sigma_y}\right) + \left(\frac{y-\mu_y}{\sigma_y}\right)^2\right\}\right]}{2\pi\sigma_x\sigma_y\sqrt{1-\rho^2}} \quad (1)$$

where $\rho(=\sigma_{xy}/\sigma_x\sigma_y)$ is the correlation coefficient, $\sigma_{xy}=\langle XY\rangle-\langle X\times Y\rangle$, $\sigma_x^2=\langle X^2\rangle-\langle X\rangle^2$, $\sigma_y^2=\langle Y^2\rangle-\langle Y\rangle^2$, $\mu_x=\langle X\rangle$, and $\mu_y=\langle Y\rangle$. In these definitions capital letters denote random variables and a bracket denotes the mean operator as in $$\langle f(X, Y)\rangle = \int_{-\infty}^{+\infty} f(x, y)p(x, y)\,dx\,dy. \quad (2)$$

In the following, the subscripts "1", "2", and "m" are used to denote quantities associated with the two statistically independent bi-variate normals "1" and "2" and the merged bivariate normal "m." Thus, the position coordinates $(X_1,Y_1)$ are described by $p_1(x,y)$, given by (1) with $\mu_{1x}, \mu_{1y}, \sigma_{1x}^2, \sigma_{1y}^2$, and $\sigma_{1xy}$ (or $\rho_1$) and $(X_2,Y_2)$ by $p_2(x,y)$, likewise given by (1), with $\mu_{2x}, \mu_{2y}, \sigma_{2x}^2, \sigma_{2y}^2$, and $\sigma_{2xy}$ (or $\rho_2$). We assume that random variables $X_1$ and $Y_1$ are statistically independent of variables $X_2$ and $Y_2$ so that, e.g., $\langle X_1 X_2 \rangle = \langle X_1 \times X_2 \rangle = \mu_{1x}\mu_{2x}$.

Points "1" and "2" are merged into the single point "m" described by the probability density $P_m(x,y)$ given by (1) with parameters $\mu_{mx}, \mu_{my}, \sigma_{mx}^2, \sigma_{my}^2$, and $\sigma_{mxy}$. These parameters are, by definition, identical to the means, variances, and covariance of the pooled probability density $[p_1(x,y)+p_2(x,y)]/2$, i.e., $p_m(x,y)=[p_1(x,y)+p_2(x,y)]/2$ through second order moments. Thus, $\mu_{mx}$ is defined by $$\mu_{mx} = \left\langle \frac{(X_1+X_2)}{2} \right\rangle = \frac{\mu_{1x}+\mu_{2x}}{2} \tag{3}$$

and, also $$\mu_{my} = \frac{\mu_{1y}+\mu_{2y}}{2}. \tag{4}$$

In similar fashion $$\sigma_{mx}^2 = \left\langle \frac{1}{2}(X_1+X_2)^2 \right\rangle - \left(\frac{\mu_{1x}+\mu_{2x}}{2}\right)^2 \tag{5}$$

$$= \frac{(\sigma_{1x}^2+\sigma_{2x}^2)}{2} + \frac{(\mu_{1x}-\mu_{2x})^2}{4},$$

$$\sigma_{my}^2 = \frac{(\sigma_{1y}^2+\sigma_{2y}^2)}{2} + \frac{(\mu_{1y}-\mu_{2y})^2}{4}, \tag{6}$$

and $$\sigma_{mxy} = \frac{(\sigma_{1xy}+\sigma_{2xy})}{2} + \frac{(\mu_{1x}-\mu_{2x})(\mu_{1y}-\mu_{2y})}{4}. \tag{7}$$

Figure 1:
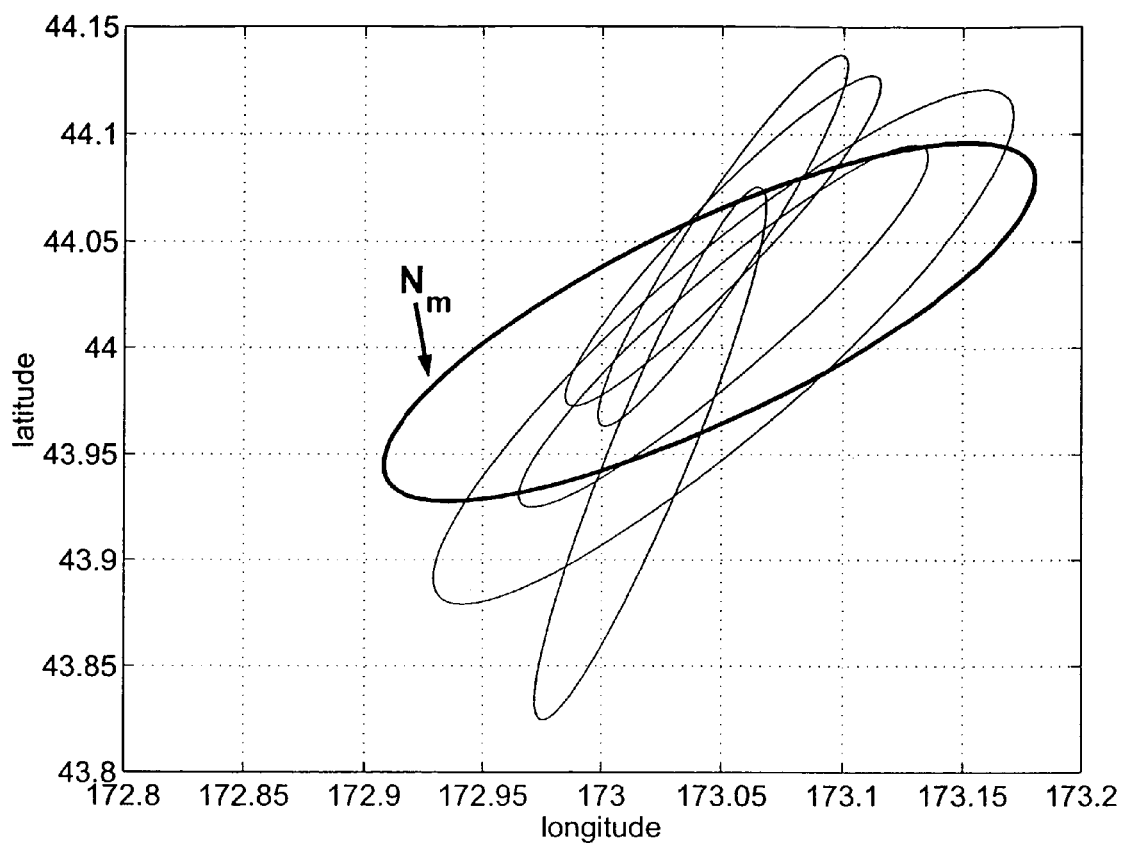
FIG. 1 depicts a data fusion of imprecise geospatial data in the form of error ellipses, according to an embodiment of the present invention.

As one might expect, the separations of the means, $(\mu_{1x}-\mu_{2x})$ and $(\mu_{1y}-\mu_{2y})$, of the variables "1" and "2" contribute to the variances and covariance of the merged variable. FIG. 1 illustrates the result of merging two error ellipses.

II. Whether to Merge Two Error Ellipses

In deciding whether to merge two error ellipses we compare the entropy or, equivalently, the "missing information" of the two error ellipses with the entropy of the single ellipse into which the two would be merged. Indeed, it is only comparative entropies that can be coherently defined for continuous random variables. The so-called "self-entropy" of a continuous bi-normal random variable with probability density $p(x,y)$, that is, $-\langle \ln[p(x,y)] \rangle$ or $$-\int_{-\infty}^{+\infty} p(x,y)\ln[p(x,y)]\,dx\,dy$$

has been severely criticized not only as capable of assuming negative values but also as being dimensionally indeterminate as is disclosed in Smith, J. D. H. "Some Observations on the Concepts of Information-Theoretic Entropy and Randomness," *Entropy*, 3, 1-11(2001), the contents of which are incorporated herein by reference. Neither of these two properties has a natural information-theoretic interpretation.

For this reason another quantity the relative entropy of one ellipse with respect to another is exploited as disclosed in Jumarie, G., *Relative Information*, (Springer-Verlag, Berlin, 1990) p. 36, the contents of which are incorporated herein by reference. In particular, the relative entropy of ellipse "1" with respect to a reference ellipse "0" is defined by $$S(1,0) = -\int p_1(x,y)\ln\left[\frac{p_1(x,y)}{p_0(x,y)}\right]dx\,dy \tag{8}$$

where, of course, the primary and reference probability densities $p_1(x,y)$ and $p_0(x,y)$ must be normalized and positive definite on the same domain. Since regions of the domain for which $p_1(x,y)>p_0(x,y)$ contribute negatively to the relative entropy and regions for which $p_1(x,y)<p_0(x,y)$ contribute positively, negative values of $S(1,0)$ are associated with a relatively small and positive values with a relatively large error ellipse "1" compared to the area of the reference ellipse "0." In short, the reference ellipse establishes a metric with which the entropy of a random variable is quantified.

The relative entropy generated when ellipse "1" and "2" are merged into a single ellipse "m" is given by the difference, $$\Delta S = S(m,0) - S(1,0) - S(2,0), \tag{9}$$

between the relative entropy of the merged ellipse and the sum of the relative entropies of the two original ellipses. $\Delta S \geq 0$ for any reference ellipse "0" and also that $\Delta S$ is minimum when the merged ellipse "m" is identified with the reference ellipse "0" or vice-versa. This optimization is adapted, i.e., "0"="m". Since the entropy of an ellipse relative to itself necessarily vanishes, e.g., $S(m,m)=0$, equation (9) becomes $$\Delta S = -S(1,m) - S(2,m). \tag{10}$$

Equation (10) is, in turn, equivalent to $$\Delta S = \int p_1(x,y)\ln[p_1(x,y)]dx\,dy + \int p_2(x,y)\ln[p_2(x,y)]dx\,dy - \int [p_1(x,y)+p_2(x,y)]\ln[p_m(x,y)]dx\,dy. \tag{11}$$

However, since the moments, through second order, of $P_m(x,y)$ are, by definition, identical to the moments, through second order, of $[p_1(x,y)+p_2(x,y)]/2$, (11) can also be written as $$\Delta S = -2\int p_m(x,y)\ln[p_m(x,y)]dx\,dy + \int p_1(x,y)\ln[p_1(x,y)]dx\,dy + \int p_2(x,y)\ln[p_2(x,y)]dx\,dy \tag{12}$$

Thus, the entropy generated $\Delta S$ by merging two ellipses is the difference between the self-entropy associated with two, independent, merged ellipses minus the self-entropy associated with the two original ellipses. Given that each of the probability densities, $p_1(x,y), p_2(x,y)$, and $p_m(x,y)$, is that of a correlated bi-variate normal, (12) becomes $$\Delta S = \ln\left[\frac{\sigma_{mx}^2 \sigma_{my}^2(1-\rho_m^2)}{\sigma_{1x}\sigma_{1y}\sqrt{1-\rho_1^2}\,\sigma_{2x}\sigma_{2y}\sqrt{1-\rho_2^2}}\right]. \tag{13}$$

The argument of the natural logarithm in (13) is the ratio of the square of the area of the merged ellipse $A_m^2 = [\pi\sigma_{mx}\sigma_{my}\sqrt{1-\rho_m^2}]^2$ to the product of the areas of the unmerged ellipses $A_1 = \pi\sigma_{1x}\sigma_{1y}\sqrt{1-\rho_1^2}$ and $A_2 = \pi\sigma_{2x}\sigma_{2y}\sqrt{1-\rho_2^2}$. The criteria that ellipses are merged only when the entropy generated, $\Delta S$, is less than or equal to a critical amount $\Delta S_{crit}$, i.e., only when $\Delta S \leq \Delta S_{crit}$, reduces to a condition on the ratio $A_m^2/(A_1 A_2)$, i.e., $$\frac{\sigma_{mx}^2 \sigma_{my}^2 (1 - \rho_m^2)}{\sigma_{1x}\sigma_{1y}\sqrt{1-\rho_1^2}\,\sigma_{2x}\sigma_{2y}\sqrt{1-\rho_2^2}} \le R_{crit} \quad (14)$$

where $R_{crit} = \exp\{\Delta S_{crit}\}$. The actual numerical value of the critical ratio of areas $R_{crit}$ regulates the degree of similarity required for merging. Thus, the smaller $R_{crit}$ (recall that $R_{crit} \ge 1$), the more similarity is required for merging; the larger $R_{crit}$ the less similarity is required.

III. Merging More Than Two Error Ellipses

Suppose we wish to test whether or not a group of n ellipses representing n statistically independent bi-variate normal variables should be clustered and merged. The generalization from two to many ellipses is quite straightforward. First, we determine the parameters describing the merged ellipse in terms of the parameters describing the n unmerged ellipses via the data-pooling algorithm. Thus, $$\mu_{mx} = \left\langle \frac{1}{n}\sum_{i=1}^{n} X_i \right\rangle = \frac{1}{n}\sum_{i=1}^{n} \mu_{ix} \quad (15)$$

and $$\mu_{my} = \frac{1}{n}\sum_{i=1}^{n} \mu_{iy}. \quad (16)$$

Furthermore, $$\sigma_{mx}^2 = \left\langle \frac{1}{n}\sum_{i=1}^{n} (X_i - \mu_x)^2 \right\rangle \quad (17)$$

$$= \frac{1}{n}\sum_{i=1}^{n} \sigma_{ix}^2 + \frac{1}{n}\sum_{i=1}^{n} (\mu_{ix} - \mu_x)^2, \quad (18)$$

$$\sigma_{my}^2 = \left\langle \frac{1}{n}\sum_{i=1}^{n} (Y_i - \mu_y)^2 \right\rangle \quad (19)$$

$$= \frac{1}{n}\sum_{i=1}^{n} \sigma_{iy}^2 + \frac{1}{n}\sum_{i=1}^{n} (\mu_{iy} - \mu_y)^2,$$

and $$\sigma_{mxy} = \frac{1}{n}\sum_{i=1}^{n} \sigma_{ixy} + \frac{1}{n}\sum_{i=1}^{n} (\mu_{ix} - \mu_x)(\mu_{iy} - \mu_y). \quad (20)$$

The criteria for merging then becomes $$S(m, 0) - \sum_{i=1}^{n} S(i, 0) \le S_{crit}. \quad (21)$$

On minimizing the entropy generated by merging, i.e., on identifying the merged ellipse with the reference ellipse, i.e., "m"="0", and (21) becomes $$\sum_{i=1}^{n} \int p_i(x,y) \ln\left[\frac{p_i(x,y)}{p_m(x,y)}\right] dx\,dy \le S_{crit} \quad (22)$$

or, since, through second order moments, $$p_m = (1/n)\sum_{i=1}^{n} p_i, \quad (23)$$

$$\int \sum_{i=1}^{n} p_i(x,y) \ln[p_i(x,y)] dx\,dy -$$

$$n \int p_m(x,y) \ln[p_m(x,y)] dx\,dy \le S_{crit}.$$

Given that the $p_1(x,y)$ and $p_m(x,y)$ represent bi-variate normals, (23) becomes $$\ln\left[\frac{\sigma_{mx}^{n/2} \sigma_{my}^{n/2} (1 - \rho_m^2)^{n/2}}{\prod_{i=1}^{n} \sigma_{ix}\sigma_{iy}\sqrt{(1-\rho_i^2)}}\right] \le S_{crit} \quad (24)$$

which is equivalent to $$\frac{\sigma_{mx}^{n/2} \sigma_{my}^{n/2} (1 - \rho_m^2)^{n/2}}{\prod_{i=1}^{n} \sigma_{ix}\sigma_{iy}\sqrt{(1-\rho_i^2)}} \le R_{crit}. \quad (25)$$

The later is the generalization of criterion (14) to the case of merging n ellipses.

FIG. 1 depicts an example showing five error ellipses representing five location measurements. From these measurements, the most probable location of a target is determined by constructing a merged error ellipse Nm as discussed above. The loss of information reflected in the merging of the measurements into one error ellipse is determined to be: $\Delta S = 5.14$. If the loss of information is small relative to a known threshold, the target would have a 95% probability of being within Nm and the most probable position of the target would be at its center.

Figure 2:
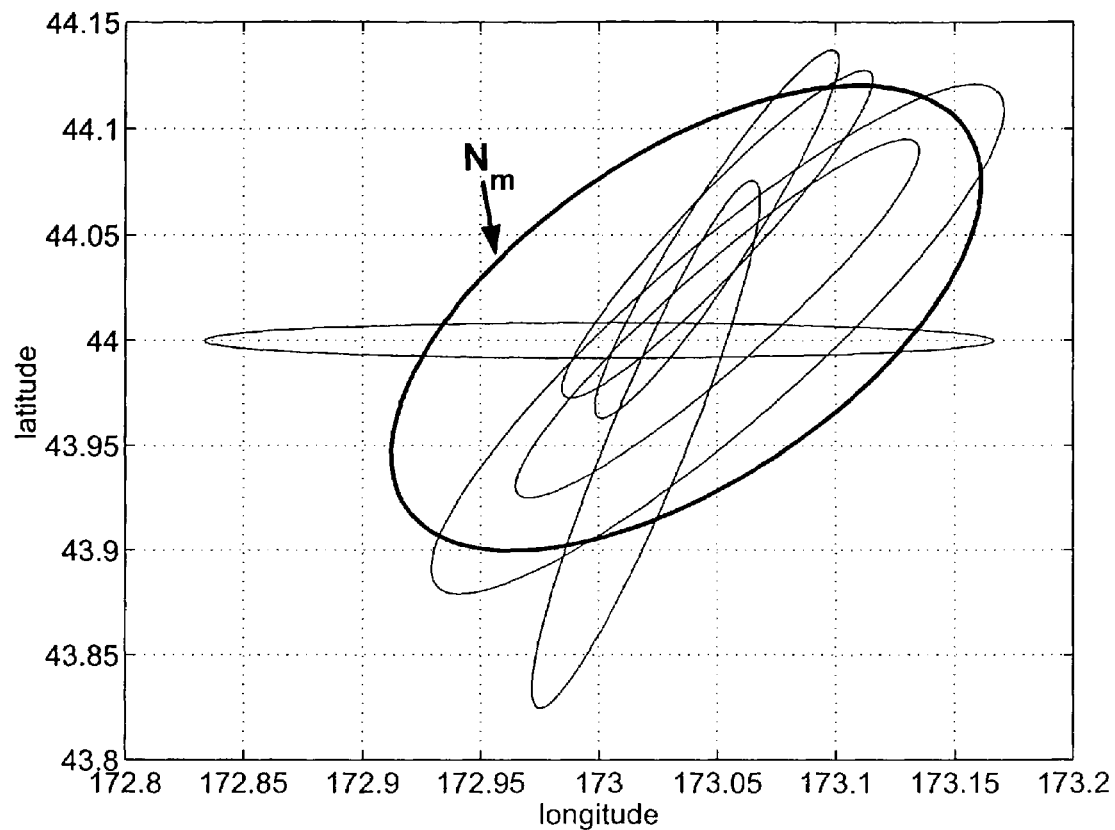
FIG. 2 depicts a data fusion of imprecise geospatial data in the form of error ellipses where one error ellipse has a different orientation, size and shape according to an embodiment of the present invention.

FIG. 2 depicts an example showing six error ellipses (five of them from the dataset of FIG. 1). The sixth ellipse has a different orientation, center and shape than the other ellipses. Also shown is the merged ellipse of the dataset of FIG. 2, again denoted by Nm The entropy increase in this case is calculated to be $\Delta S = 9.62$, suggesting that the loss of information by merging this sixth, somewhat different, ellipse in the dataset may be significant. In some applications, the relatively large size of Nm and large value of $\Delta S$ may be above a given empirical threshold, resulting in a measurement being discarded or perhaps being identified with another target.

While the present invention has been described in connection with the preferred embodiments of the various figures, it is to be understood that other similar embodiments may be used or modifications and additions may be made to the described embodiment for performing the same function of the present invention without deviating therefrom. For example, the invention may be implemented by a general purpose computer having a processor, memory and computer program instructions stored therein. The equations, for example, may be implemented in a computer program product executed by the computer which causes the computer to process information received from, for example a network, a database or other memory, and/or sensors. The present invention should not be limited to any single embodiment, but rather construed in breadth and scope in accordance with the recitation of the appended claims.

What is claimed is:

1. An information theoretic method of clustering and merging bi-variate normal data comprising the steps of:
    storing bi-variate normal data in a memory;
    processing the data using a processor coupled to the memory to cluster the data into two or more error ellipses; and
    further processing the data using the processor to merge the data into a single replacement error ellipse if the information lost in the merging process is sufficiently small.

2. The method according to claim 1, further comprising:
    processing the data to determine a change in entropy associated with merging the ellipses.

3. The method according to claim 2, wherein the change in entropy is compared with a predetermined threshold to determine whether information lost in the merging process is sufficiently small.

4. The method according to claim 3, further comprising:
    determining the most probable location of a target based on the merging.

5. The method according to claim 1, wherein the data is one of global positioning system data; geographic information system data, bioinformatics data and pattern recognition data.

6. A computer program product comprising a computer usable medium having computer program logic stored therein, wherein the computer program logic comprises:
    clustering logic for causing a computer to cluster data that includes associated error into two or more error ellipses; and
    merging logic for causing the computer to merge the data into a single replacement error ellipse if the information lost in the merging process is sufficiently small.

7. The computer program product according to claim 6, further comprising:
    determining logic for causing the computer to determine a change in entropy associated with merging the ellipses.

8. The computer program product according to claim 7, wherein the change in entropy is compared with a predetermined threshold to determine whether information lost in the merging process is sufficiently small.

9. The computer program product according to claim 8, further comprising:
    determining logic for causing the computer to determine the most probable location of a target based on the merging.

10. The computer program product according to claim 6, wherein the data is one of global positioning system data; geographic information system data, bioinformatics data and pattern recognition data.

* * * * *